US00PP34809P3

(12) United States Plant Patent
Olesen

(10) Patent No.: US PP34,809 P3
(45) Date of Patent: Dec. 13, 2022

(54) ROSE PLANT NAMED 'POULPAR128'

(50) Latin Name: *Rosa hybrida*
Varietal Denomination: Poulpar128

(71) Applicant: Mogens Nyegaard Olesen, Fredensborg (DK)

(72) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 17/300,634

(22) Filed: Sep. 7, 2021

(65) Prior Publication Data

US 2022/0104417 P1 Mar. 31, 2022

(30) Foreign Application Priority Data

Sep. 21, 2020 (QZ) ..... PBR 2020/2271

(51) Int. Cl.
*A01H 5/02* (2018.01)
*A01H 6/74* (2018.01)

(52) U.S. Cl.
USPC ..... Plt./121
CPC ..... *A01H 6/749* (2018.05)

(58) Field of Classification Search
USPC ..... Plt./121, 128
CPC ..... A01H 5/022
See application file for complete search history.

*Primary Examiner* — Kent L Bell

(57) ABSTRACT

A new garden rose plant of the Miniature class which has abundant, light pink flowers and attractive foliage. This new and distinct variety has shown to be uniform and stable in the resulting generations from asexual propagation.

2 Drawing Sheets

Botanical designation: *Rosa hybrida.*

Variety denomination: 'Poulpar128'.

This application claims priority to Plant Breeder's Rights Application Number 2020/2271, which was filed at the Community Plant Variety Rights Office in the European Union on Sep. 21, 2020, the contents of which are hereby incorporated by reference for all purposes.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2014 and the resulting seeds were planted in a controlled environment in Fredensborg, Denmark. The new variety, named 'Poulpar128', originated as a single seedling from the stated cross.

The new variety may be distinguished from its male pollen parent and female seed parent primarily by the following characteristics. The male pollen parent plant has pink flowers while the new variety has light pink flowers. The female seed parent plant grows to a height of 100 cm while the new variety grows to 26 cm height.

The objective of the hybridization of this rose variety was to create a new and distinct variety with unique qualities, such as:

1. Uniform and abundant light pink flowers;
2. Vigorous, but compact growth when propagated on its own roots;
3. Exceptional disease resistance.

This combination of qualities is not present in previously available commercial cultivars of this type, known to the inventor, and distinguish 'Poulpar128' from all other varieties of which we are aware.

As part of the rose development program, Mogens N. Olesen germinated the seeds from the aforementioned hybridization during winter of 2014 and conducted evaluations on the resulting seedlings in a controlled environment in Fredensborg, Denmark. 'Poulpar128' was selected in the spring of 2015 by the inventor as a single plant from the progeny of the aforementioned hybridization.

Asexual reproduction of 'Poulpar128' by rooted cuttings was first done by Mogens N. Olesen in the nursery in Fredensborg, Denmark in July, 2015. This initial and other subsequent asexual propagations conducted in controlled environments have demonstrated that the characteristics of 'Poulpar128' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulpar128'.

Specifically illustrated in FIG. 1 of the drawings are open flowers viewed from above and the side, flower petals detached revealing reproductive flower parts, flower buds upon opening, and sepals detached revealing receptacle.

Figure 1:
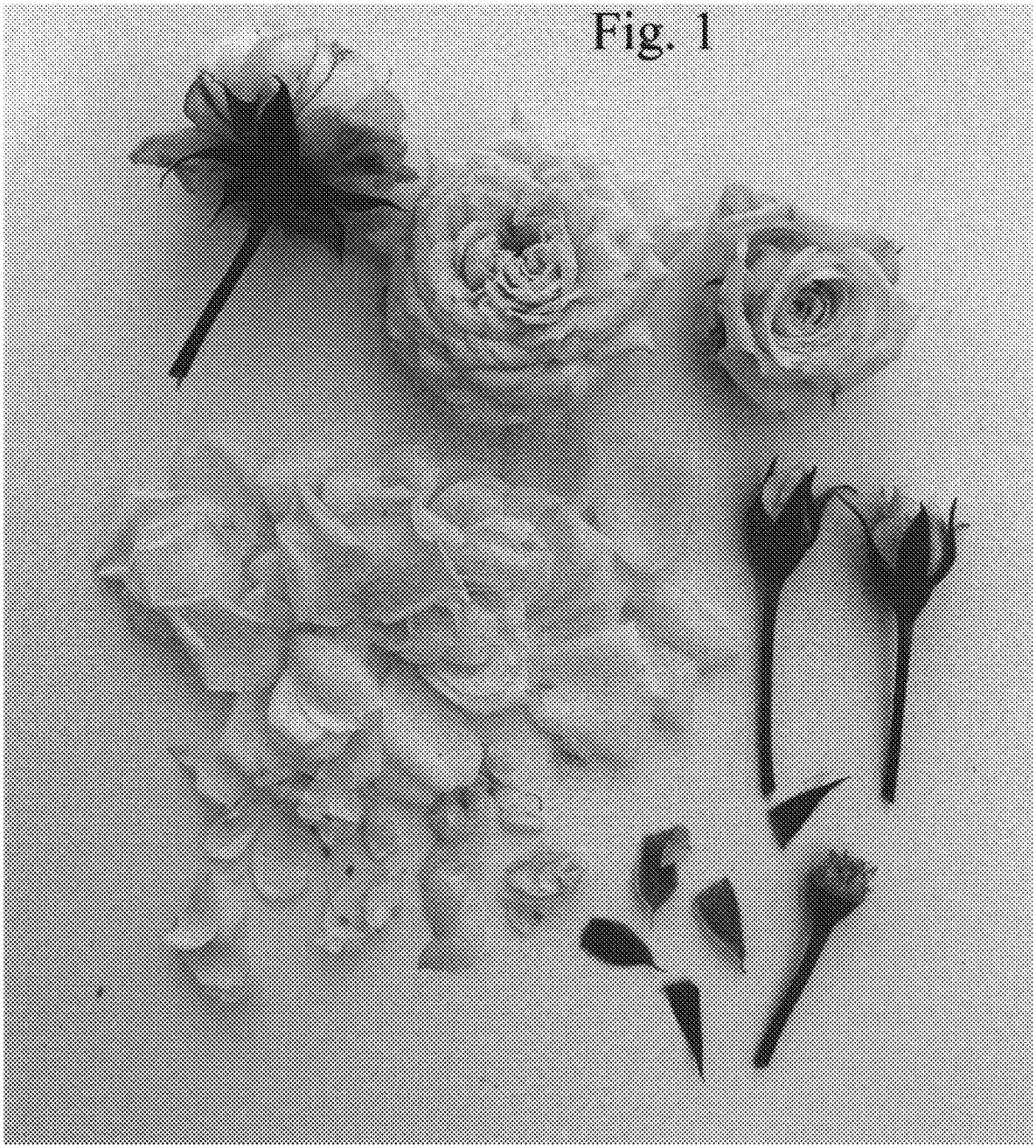
Figure 2:
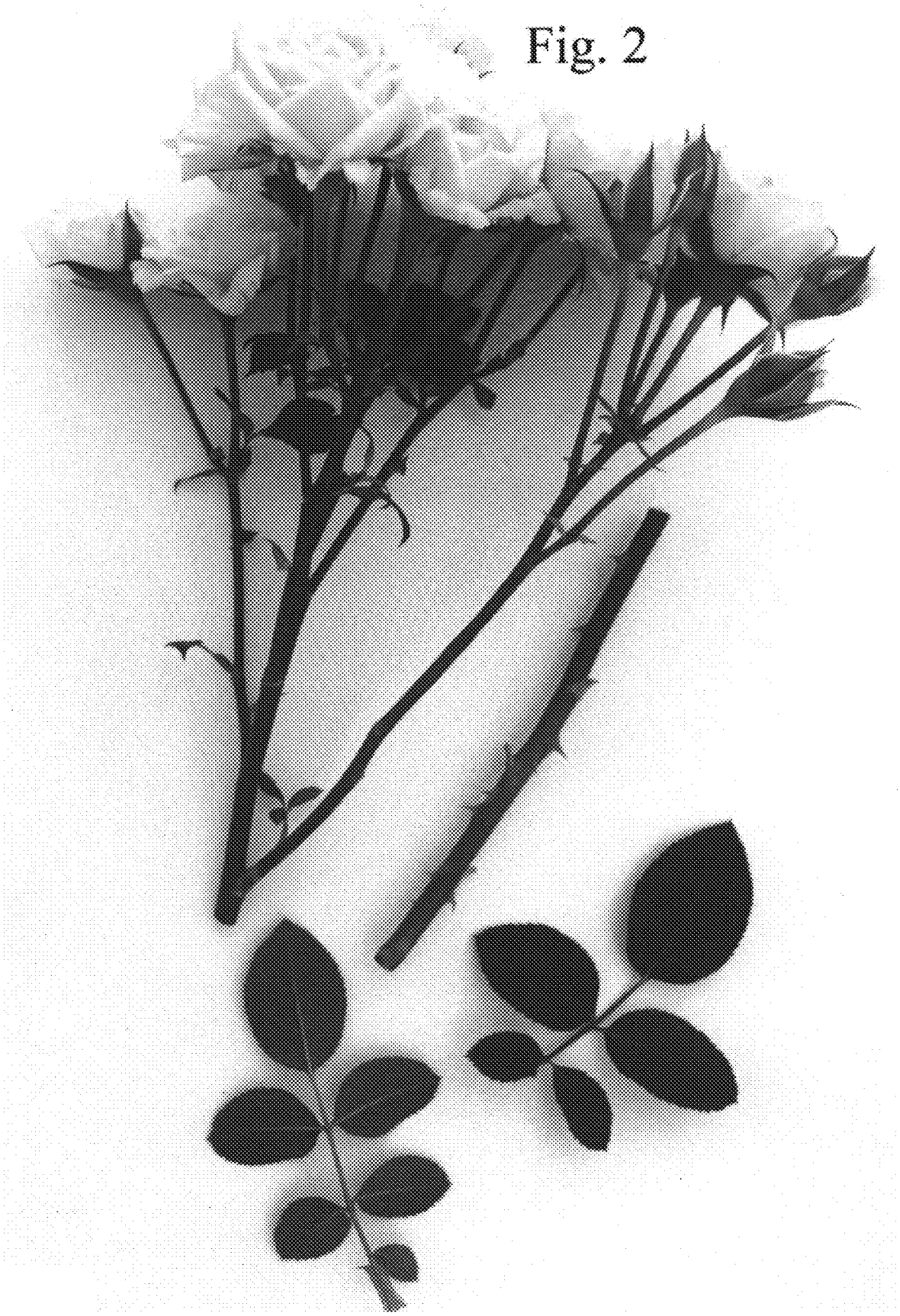

Specifically illustrated in FIG. 2 of the drawings is a bare stem exhibiting prickles, upper and lower side of mature leaves, a cluster of flowers on a flowering branch. Plants shown are 2 years of age.

DETAILED DESCRIPTION OF THE VARIETY

The following is a description of 'Poulpar128', as observed in its growth in a glasshouse in Odense Denmark. Plants were grown in 19 cm pots, for a period of 4 months.

For a comparison, several physical characteristics of the rose variety 'Poulpar094', U.S. Plant Pat. No. 30,382 dated Apr. 16, 2019 are compared to 'Poulpar128' in Chart 1.

CHART 1

| | 'Poulpar128' | 'Poulpar094' |
|---|---|---|
| Petal Count | 45 | 40 |
| Flower Diameter | 58 mm | 75 mm |
| General Tonality of Flower Color | White Group 155A upon opening. As flowers mature the tonality changes to Red Group 49C. | Red-Purple Group 62A |

Flower and flower bud:

*Blooming habit.*—Continuous.

*Flower bud.*—Size: Upon opening, 25 mm in length from base of receptacle to end of bud. Bud diameter is 14 mm. Bud form: Ovoid. Bud color: As sepals divide petals are Orange Group 29C and Yellow-Orange Group 23D. Sepal inner surface: Color: Yellow-Green Group 146D. Surface: Lightly pubescent. Sepal outer surface: Color: Yellow-Green Group 144A. Texture: Smooth. Sepal Shape: General: Subulate. Apex: Cirrhose. Base: Flat at union with receptacle. Sepal Margin: Margins have weak foliaceous appendages on three of the five sepals. Sepal size: 26 mm long by 6 mm wide. Receptacle: Texture: Smooth. Size: 8 mm in height, 9 mm wide. Color: Yellow-Green Group 144A. Shape: Funnel. Pedicel: Surface: Smooth. Length: 36 mm. Diameter: 2 mm on average. Color: Yellow-Green Group 144A. Strength: Strong. Peduncle: Length: 1 to 10 cm. Diameter: About 3 to 4 mm. Color: Yellow-Green Group 144A. Texture: Smooth.

*Flower bud development.*—Flower buds are borne in clusters of 3 to 15 flower buds per stem.

*Flower bloom.*—Fragrance: Moderate. Duration: The blooms have a duration on the plant of approximately 19 days. Petals fall cleanly away from plant after flowers have fully matured. Size: Flower diameter is 58 mm when open. Flower depth is 25 mm. Flower shape: Rosette, very double flower with many slightly overlapping petals of different sizes. Shape of flower, side view: The upper portion is flat convex. The lower portion is concave.

*Petalage.*—Under normal conditions, flowers have about 45 petals.

*General tonality of flower.*—White Group 155A upon opening. As flowers mature the tonality changes to Red Group 49C.

*Petal color.*—Upon opening, outer petals Upper surface: White Group 155A. No petal spot. Lower surface: White Group 155A with streaks of Yellow-Green Group 145B. No petal spot. Upon opening, inner petals: Upper surface: White Group 155A. No petal spot. Lower surface: White Group 155A with streaks of Yellow-Green Group 145B. No petal spot. Basal petal spots upon opening: No distinctive coloration at the petal base observed. After opening, outer and inner petals Upper surface: White Group 155A with intonations of Red Group 49C. At the base Yellow Group 8D. Lower surface: White Group 155A with intonations of Red Group 36C. At the base Yellow Group 8D.

*Petals.*—Petal Reflex: Strong reflexed. Margin: Entire and uniform. Outer petals have no undulations. Inner petals have strong undulations. Shape: Broad and elliptic. Apex shape: Rounded. Base shape: Acute. Size: 31 mm (l)×28 mm (w). Texture: Smooth. Thickness: Average.

*Petaloids.*—Size: 16 mm (l) by 9 mm (w). Quantity: 18-20. Shape: Elliptical with an acute base and rounded apices. Color: Red Group 49C on the upper surface, with a basal petaloid spot of Yellow Group 8D. On the lower surface White Group 155A with intonations of Red Group 36C, and a basal spot of Yellow Group 8D.

*Reproductive flower parts.*—Pollen: None observed. Anthers: Size: 1.5 mm in length. Color: Yellow Group 13C. Quantity: 28 on average. Filaments: Color: Yellow Group 8A. Length: 4 mm. Pistils: Length: 6 mm. Quantity: 44 on average. Stigmas: Color: Greyed-Yellow Group 160D. Styles: Color: Red Group 51A. Location of stigmas: Even in location relative to the length of the filaments and the height of the anthers. Hips: None Observed.

Plant:

*Plant growth.*—Upright, bushy and very compact. Plants are 26 cm in height, and 32 cm wide.

*Stems.*—Color of juvenile growth: Yellow-Green Group 144B. Color of mature growth: Yellow-Green Group 144A. Length: Canes are about 12 cm from the base of the plant to the flowering portion. Diameter: About 6 mm. Internodes: On mature canes about 31 mm between nodes. Surface Texture: Young wood: Smooth. Older wood: Smooth.

*Long prickles.*—Incidence: 6 prickles per 10 cm of stem. Size: Average length of prickles on mature stems is 6 mm. Shape: Upper portion is linear. Lower portion is concave. Color: Juvenile prickles: Greyed-Yellow Group 161B. Mature prickles: Greyed-Yellow Group 161B.

*Plant foliage.*—Compound leaf: About 114 mm (l)×76 mm (w). Quantity: 3 leaves per 10 cm of stem on average. Leaf bearing angle to the stem: 45 degrees. Color of juvenile foliage: Upper side: Yellow-Green Group 144A. Lower side: Yellow-Green Group 144B. Color of mature foliage: Upper side: Yellow-Green Group 147A. Lower side: Yellow-Green Group 147B.

*Plant leaves and leaflets.*—Stipules: Size: 8 mm long, 1.5 mm wide. Quantity: 2 per compound leaf. Shape: Linear, slightly broad based with outward extending apices. Margins: Finely serrated. Color: Yellow-Green Group 146A. Petiole: Length: 21 mm. Diameter: About 2 mm. Upper surface color: Yellow-Green Group 146A. Lower surface color: Yellow-Green Group 144A. Rachis: Length: 32 mm average. Diameter: 1.5 mm. Upper surface color: Yellow-Green Group 146A. Lower surface color: Yellow-Green Group 144A. Leaflet: Quantity: Normally 5 leaflets. Margins: Serrated. Size: Terminal leaflets are about 52 mm long, 31 mm wide. Shape: Generally elliptical. Base: Rounded. Apex: Acute. Texture: Smooth. Thickness: Average. Arrangement: Odd pinnate. Venation: Reticulate. Glossiness: Not glossy.

*Disease resistance.*—Above average resistance to powdery mildew *Sphaerotheca pannosa* var. *rosae,* downy mildew *Peronospora sparsa,* rust *Phragmidium* spp., black spot *Diplocarpon rosae,* and *Botrytis cinerea* under normal growing conditions.

*Cold hardiness.*—The variety is tolerant to USDA Cold Hardiness Zone 6.

*Heat tolerance.*—The variety has been found to be suitable for climate conditions found in the American Horticulture Society heat zone 7.

*Pest resistance.*—The claimed plant is susceptible to any insect pest normally associated with roses.

I claim:

1. A new and distinct variety of rose plant of the Miniature rose class named 'Poulpar128', substantially as illustrated and described herein, due to its abundant light pink flowers, disease resistance, and extended period of bloom.

* * * * *